(12) United States Patent
Johnson et al.

(10) Patent No.: US 11,197,813 B2
(45) Date of Patent: Dec. 14, 2021

(54) TATTOO REMOVAL (71) Applicant: TatXtract LLC, Evergreen, CO (US)

(72) Inventors: Benjamin Johnson, Evergreen, CO (US); Tina Seitz, Phoenix, AZ (US)

(73) Assignee: TatXtract LLC, Evergreen, CO (US)

( * ) Notice: Subject to any disclaimer, the term of this patent is extended or adjusted under 35 U.S.C. 154(b) by 0 days.

(21) Appl. No.: 15/978,587

(22) Filed: May 14, 2018

(65) Prior Publication Data
US 2019/0343752 A1  Nov. 14, 2019

(51) Int. Cl.
| | | |
|---|---|---|
| *A61K 8/73* | (2006.01) | |
| *A61B 17/34* | (2006.01) | |
| *A61K 8/19* | (2006.01) | |
| *A61K 8/26* | (2006.01) | |
| *A61K 8/20* | (2006.01) | |
| *A61Q 1/14* | (2006.01) | |

(52) U.S. Cl.
CPC .............. *A61K 8/73* (2013.01); *A61B 17/34* (2013.01); *A61K 8/19* (2013.01); *A61K 8/20* (2013.01); *A61K 8/26* (2013.01); *A61Q 1/145* (2013.01)

(58) Field of Classification Search
None
See application file for complete search history.

(56) References Cited

U.S. PATENT DOCUMENTS

| | | | |
|---|---|---|---|
| 6,168,028 B1 * | 1/2001 | Telesca | A61K 8/0208 206/439 |
| 9,278,233 B2 | 3/2016 | Carter et al. | |
| 2007/0081962 A1 * | 4/2007 | Munshi | A61K 8/0208 424/70.14 |
| 2009/0275906 A1 * | 11/2009 | Berland | A61L 15/225 604/359 |

FOREIGN PATENT DOCUMENTS

WO   WO 2017/087932   *   4/2017

OTHER PUBLICATIONS

Kataoka et al. (JBC, vol. 277, No. 39, pp. 36825-36831 (Year: 2002).*

* cited by examiner

*Primary Examiner* — Katherine Peebles
(74) *Attorney, Agent, or Firm* — Trenner Law Firm, LLC; Mark D. Trenner (57) ABSTRACT

Tattoo removal is disclosed. In an example, a method for removing tattoo ink from skin or resolving a medical condition related to tattoo ink, includes applying a primary solution of beta glucan to a treatment area having tattooed skin. The primary solution stimulates the skin in the treatment area to enhance removal of the tattoo ink from the skin. The example method also includes coating the treatment area with a secondary solution. The secondary solution may have an absorbent material to draw in loose ink. The example method also includes disrupting a skin barrier in the treatment area by a needle or ablative device to improve penetration of at least one of the primary solution and the secondary solution.

9 Claims, 11 Drawing Sheets
(11 of 11 Drawing Sheet(s) Filed in Color)

Fig. 11

TATTOO REMOVAL

BACKGROUND

Skin tattoo are commonplace again. However, many who get a tattoo want to have it removed. Tattoo ink removal from the skin can be challenging. A common method is to use a laser. But lasers have trouble targeting with white, yellow, and sometimes green inks. Often tattoos with these colors cannot be fully removed. Even for tattoos without these colors, the laser process heats the skin and often causes scar tissue to form that can permanently trap the ink within the skin.

Hypopigmentation and hypertrophic scarring are often unacceptable outcomes of using lasers to remove tattoos. Laser may also scatter ink into Nano-particles that can spread throughout the body, which may be detrimental to a person's health since the majority of tattoo ink may contain mercury, heavy metals and plastics.

Other techniques to remove tattoos include burning the skin with acids. But this too can lead to scarring and hypopigmentation. Other techniques use saline in combination with a variety of actives that do not appear to be particularly helpful in ink removal. In most cases, these ink removal solutions require compromising the skin with needles or other devices to help product penetration. But this can disrupt the barrier and the dermal region containing the ink, potentially leading to other problems.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Tattoo removal is disclosed. In an example, a technique or method may be implemented for removing tattoo ink from skin, or resolving other medical condition related to tattoo ink. An example method includes applying a primary solution of beta glucan to a treatment area having tattooed skin. The primary solution stimulates the skin in the treatment area to enhance removal of the tattoo ink from the skin. The example method also includes coating the treatment area with a secondary solution. The secondary solution may have an absorbent material to draw in loose ink. The example method may also include disrupting a skin barrier in the treatment area by a needle or ablative device to improve penetration of at least one of the primary solution and the secondary solution.

In an example, the primary solution and/or the secondary solution includes bentonite clay. In an example, the bentonite clay may be in an amount of about 1-50%, and preferably is in an amount of about 3-7%.

In an example, the primary solution and/or the secondary solution includes Himalayan Salt. Himalayan Salt may be in an amount of about 1-50%, and preferably is in an amount of about 5-10%.

In an example, the primary solution and/or the secondary solution has a pH of about 8-10.

Before continuing, it is noted that as used herein, the terms "includes" and "including" mean, but is not limited to, "includes" or "including" and "includes at least" or "including at least." The term "based on" means "based on" and "based at least in part on."

It is also noted that the examples described herein are provided for purposes of illustration, and are not intended to be limiting. Other devices and/or device configurations may be utilized to carry out the operations described herein.

In addition, the operations shown and described herein are provided to illustrate example implementations. It is noted that the operations are not limited to the ordering shown. Still other operations may also be implemented.

Topical techniques for tattoo removal are disclosed. In an example, three distinguishing approaches of the techniques described herein help pull ink out of the skin.

In an example, a solution is provided with beta glucan to activate macrophages. Macrophages are scavengers of the skin and aid in the ink removal process. The primary solution may include a special form of beta glucan that resembles what is found on yeast cell walls. By including this beta glucan in the ink removal solution creates what appears to the skin to be a yeast infection. As such, the solution triggers increased macrophage activity in the skin.

To be clear, this is not an infection in any way. Nor does the solution compromise the wound environment. The goal is to create the most ink removal with the least amount of trauma to the skin. This improves patient compliance, wound healing, and ultimately, we have found that more ink is removed with each application because the skin is operating in a uncompromised, highly efficient way.

In an example, a solution is provided with bentonite clay. Bentonite acts as a binder for ink that has been loosened from the skin. Bentonite clay has negatively charged molecules. Most toxins and heavy metals that are found in most tattoo inks (e.g., iron oxide, mercury, cadmium, lead and benzene), have positively charged molecules. This allows the two to bind together easily and stay united during the ink removal process.

Bentonite clay also has a special ability to act as an antibiotic treatment when applied topically to the skin. The clay can help to calm skin infections and speed up healing time of wounds, with its naturally occurring trace mineral content.

In addition, bentonite is shown to reduce scar formation. Clay is relatively harmless to the skin, primarily because it is discarded during the scab formation process. The wound healing component maintains a low risk of scar formation.

A secondary solution may also be implemented in the tattoo removal techniques. In an example, use of a charcoal and clay mask immediately after the first solution is rubbed into the skin, can dramatically improve the results. The underlying basis is the clay and charcoal that draws the ink to the surface more efficiently.

The techniques described herein, including the solution(s), are heading, and safe to be used around the eyes or other sensitive areas. This helps in treating individuals who have an allergic response the ink.

In an example, a method for removing tattoo ink from skin or resolving a medical condition related to tattoo ink includes applying a primary solution of beta glucan to a treatment area having tattooed skin. The primary solution stimulates the skin in the treatment area to enhance removal of the tattoo ink from the skin. In an example, the method also includes disrupting a skin barrier in the treatment area by a needle or ablative device to improve penetration of the primary solution.

In an example, the primary solution includes bentonite clay. Bentonite clay may be in an amount of about 1-50%. Preferably, the bentonite clay is in an amount of about 3-7%.

In an example, the primary solution further includes Himalayan Salt. Himalayan Salt may be in an amount of about 1-50%. Preferably, the Himalayan Salt is in an amount of about 5-10%.

In an example, the primary solution has a pH of about 8-10.

The method may also include coating the treatment area with a secondary solution. The secondary solution may include an absorbent material to draw in loose ink.

In an example, the secondary solution includes clay. The clay may be bentonite clay. Bentonite clay may be in an amount of about 1-50%. Preferably, the bentonite clay is in an amount of about 5-10%.

In an example, the secondary solution includes charcoal. Charcoal may be in an amount of about 1-50%. Preferably, the charcoal is in an amount of about 1-5%.

In an example, the solution(s) may include variations of salt, including but not limited to, sea salt, Himalayan salt, or other salt or salt-containing component.

In an example, the process further includes the solution(s) and/or combination of solution(s) removing heavy metals associated with tattoo ink in surrounding tissue.

In an example, the secondary solution has a pH of about 8-10.

The following are illustrative examples applying the solution(s) according to the techniques described herein. These are not intended to be limiting in any regard.

Figure 1:
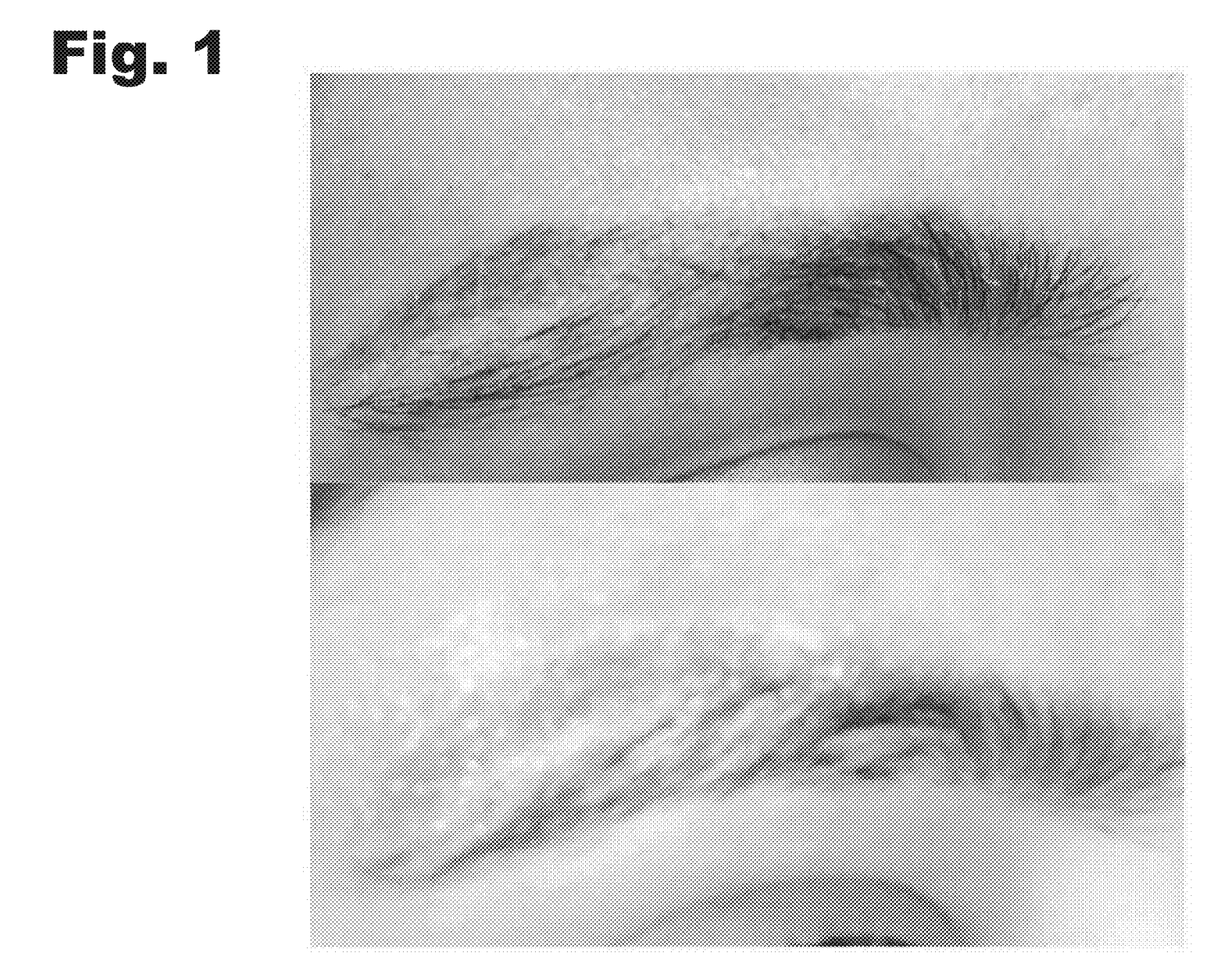
FIG. 1 are before and after images that show before and after treatment of the eyebrow tattoo, according to the techniques described herein.

FIG. 1 are before and after images that show before and after treatment of the eyebrow tattoo, according to the techniques described herein. The results show 95% removal after a single treatment. The "after" photo shows healing two weeks post treatment (new pink skin is free from any scarring).

Figure 2:
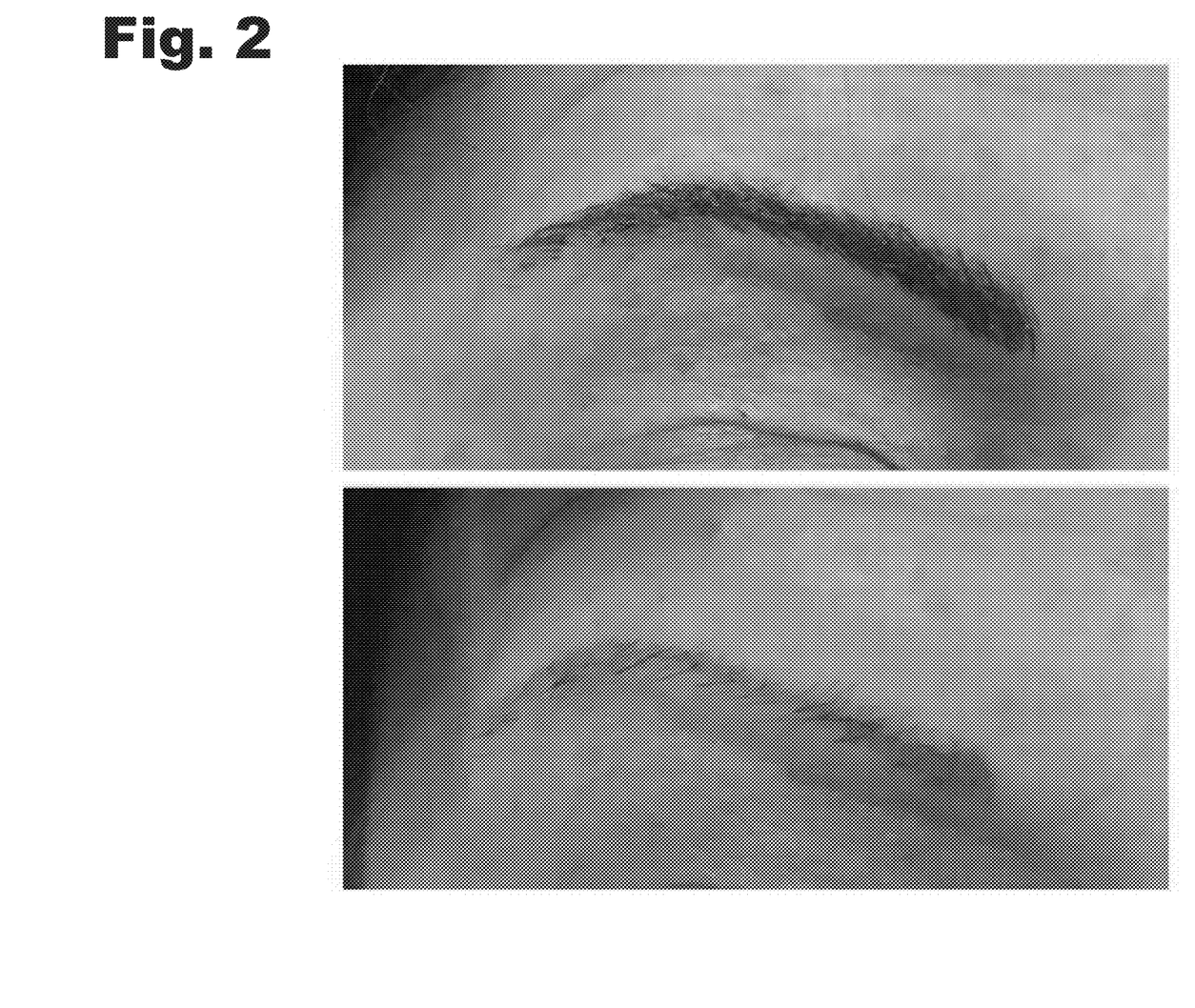
FIGS. 2-4 are before and after images that show 95% removal of an eyebrow tattoo after one treatment according to the techniques described herein.
Figure 3:
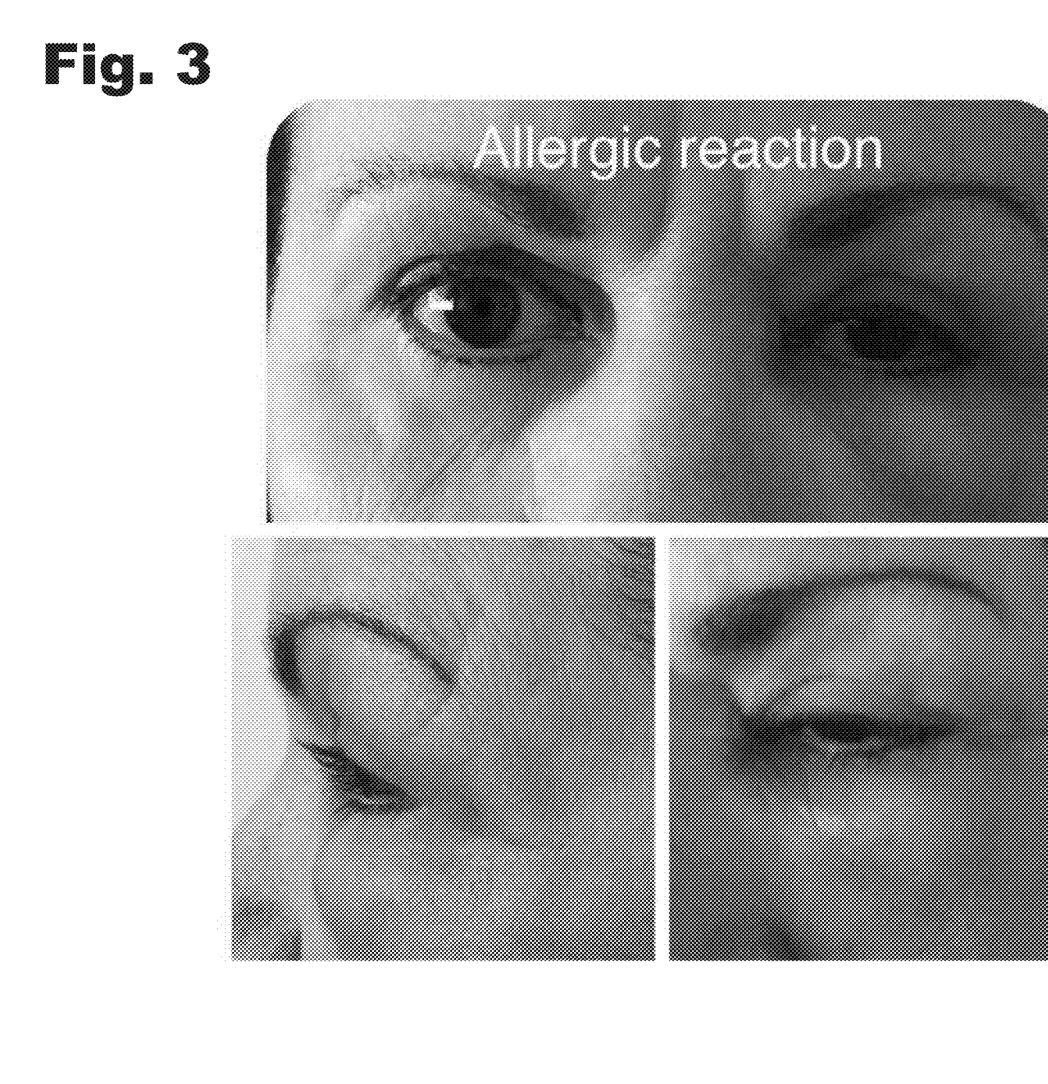
Figure 4:
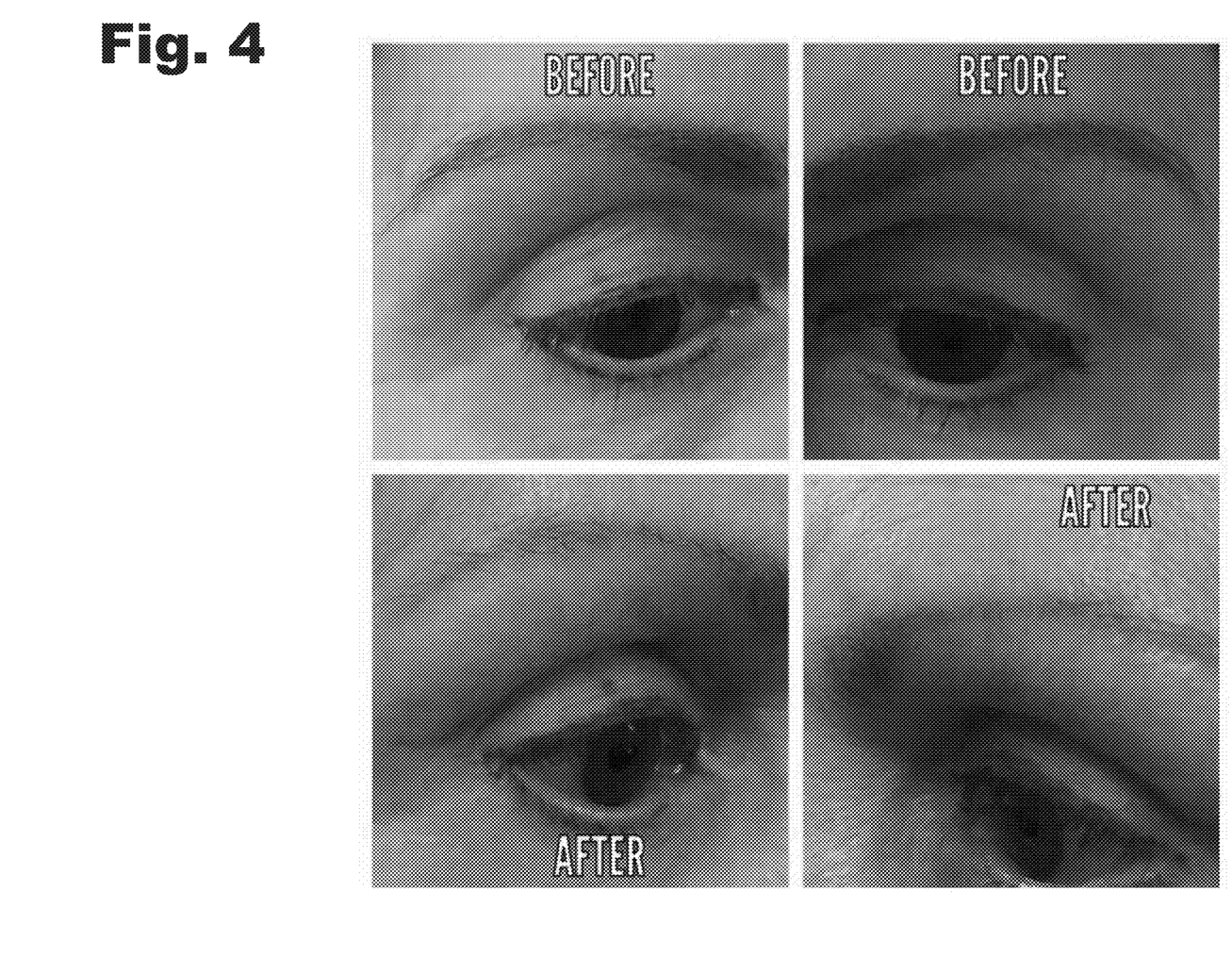

FIGS. 2-4 are before and after images that show 95% removal of an eyebrow tattoo after one treatment according to the techniques described herein. In FIG. 3, the patient had experienced an allergic reaction to her eyebrow and eyeliner tattoo ink for a period of two years, reoccurring in five-week intervals. Since laser was not an option for the condition steroids, were her only choice to control symptoms, until use of the techniques described herein. FIG. 4 shows the patient after one treatment. The reactions subsided and 95% of the tattoo ink was removed.

FIGS. 5-11 illustrate an example treatment procedure according to the treatment techniques described herein for tattoo removal.

According to the techniques described herein, the treatment may include an application of response serum that has been applied after the needling of the tattoo. In an example, an occlusive film may be applied for product penetration, followed by warm gauze applied to dilate the blood vessels. The treatment process then includes applying the second solution of ink binding mask to draw out ink and toxins to speed the healing process. It is noted that the techniques has an average treatment of between about 3-6 weeks, with about 6 weeks healing time in between treatments.

Figure 5:
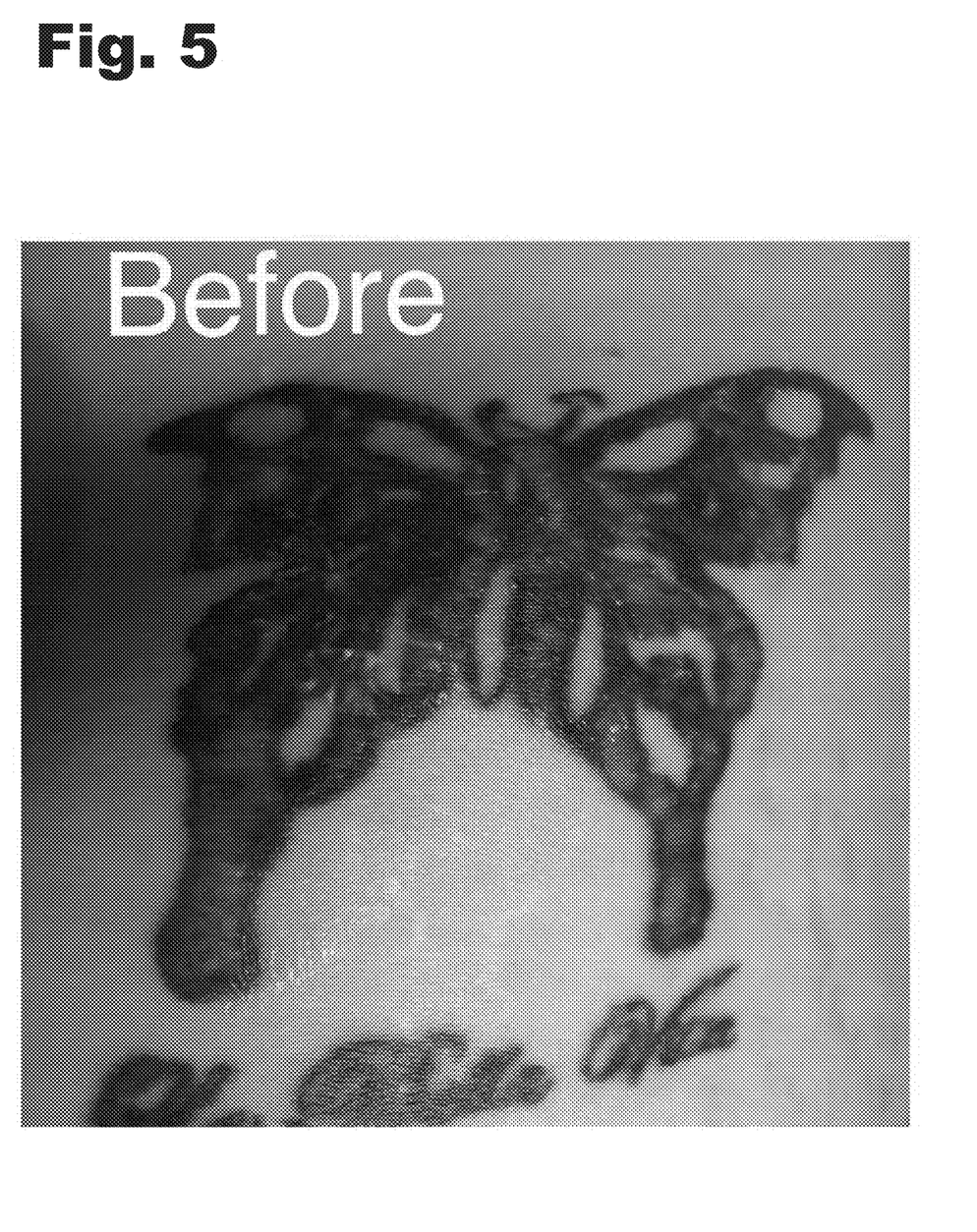
FIGS. 5-11 illustrate an example treatment procedure according to the treatment techniques described herein for tattoo removal.

FIG. 5 is a before picture of the tattoo being treated. At this point, a topical numbing agent is applied to tattoo for 20 minutes.

Figure 6:
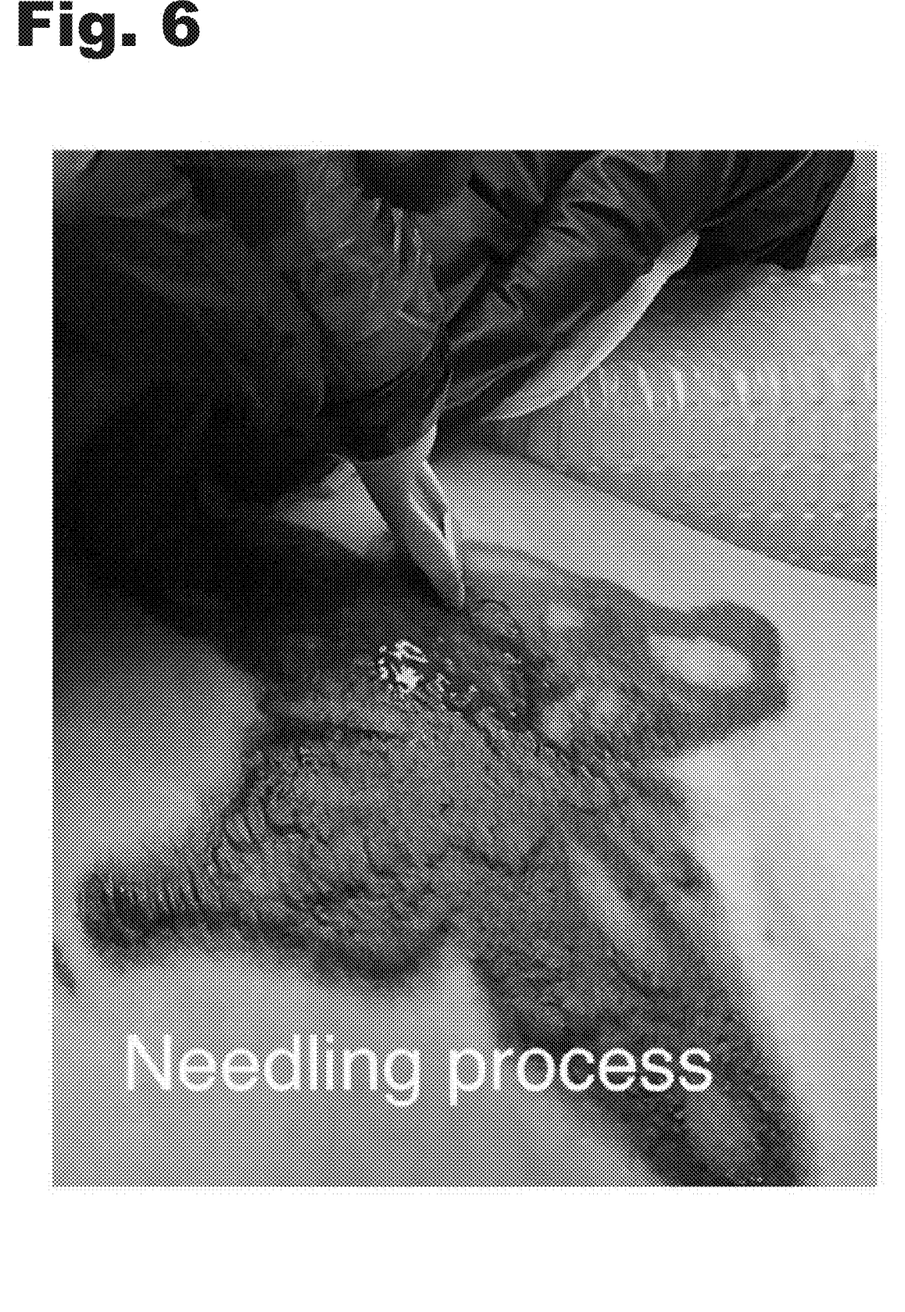

In FIG. 6, the first step of the removal process is to needle the treated area, while dipping the needle into the primary solution containing the beta glucan. This activates an immune response of the macrophage cells, continuation of this process until the desired response has occurred; approximately 3-6 passes over treated area.

Figure 7:
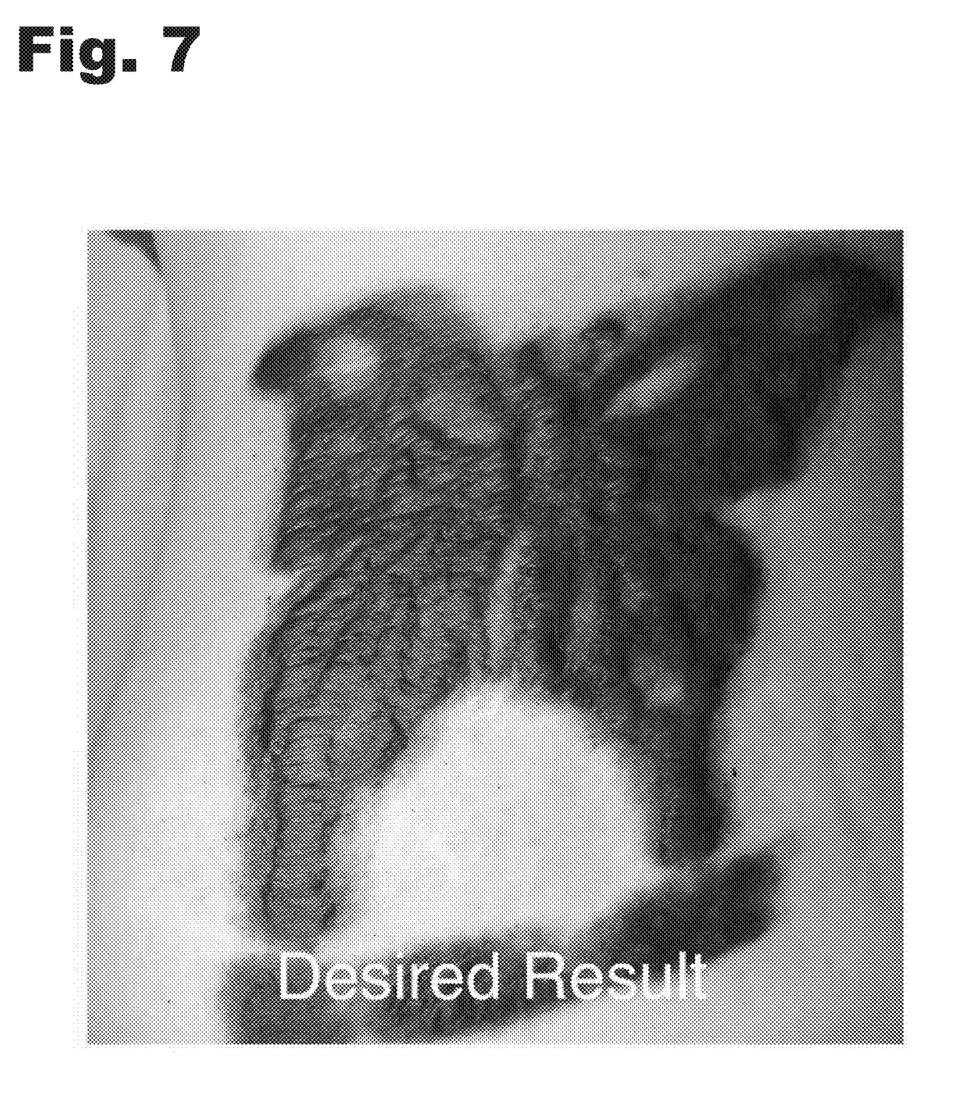

In FIG. 7, the final result appears raised or 3 dimensional in nature.

Figure 8:
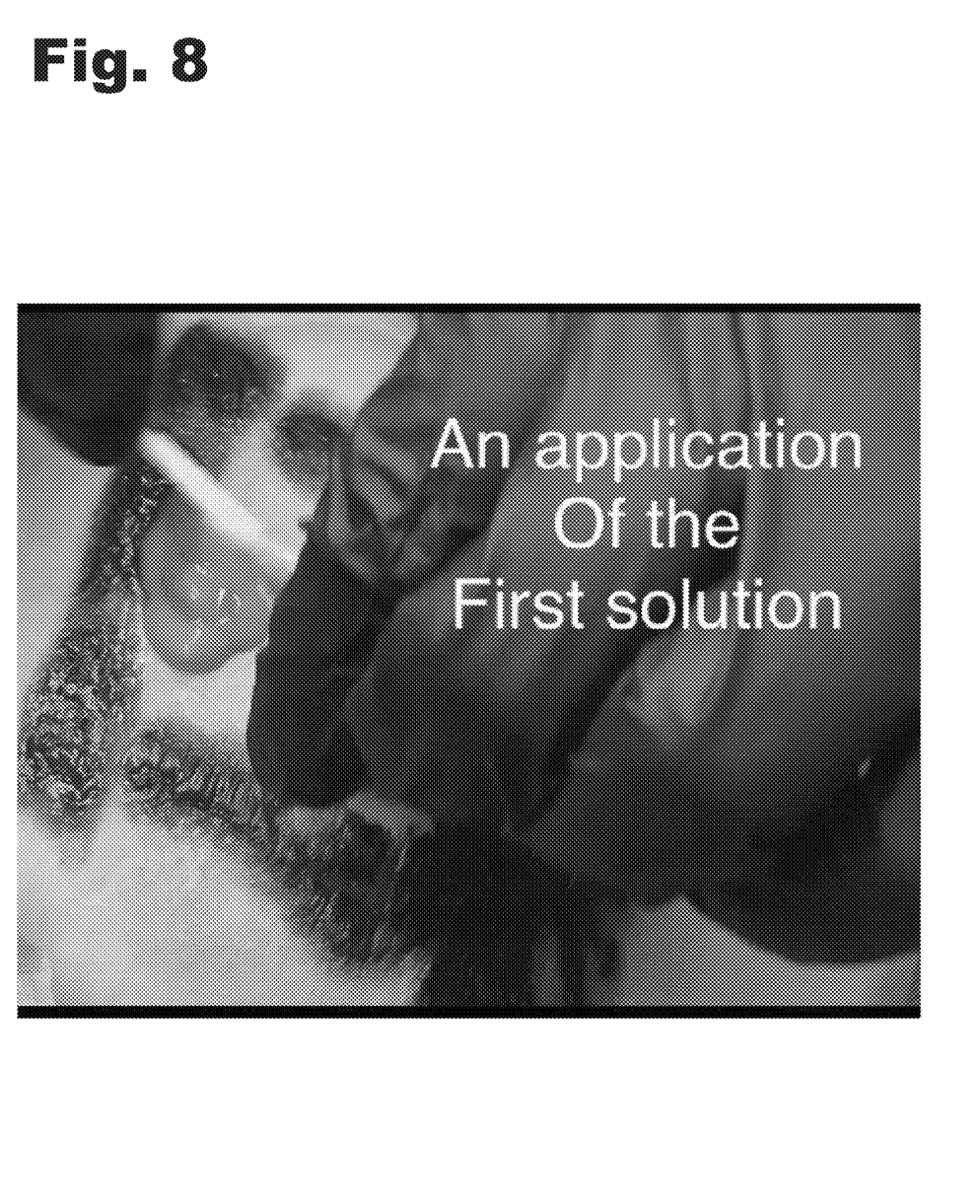

In FIG. 8, the second step requires an application of the primary solution containing the beta glucan, bentonite clay and Himalayan Salt (or saline). This step stimulates more macrophage activity, while sustaining its own subtle electromagnetic field (negatively charged particles), having extremely powerful absorption properties to attract and hold to the skins surface the tattoo ink, heavy metals and toxins.

Figure 9:
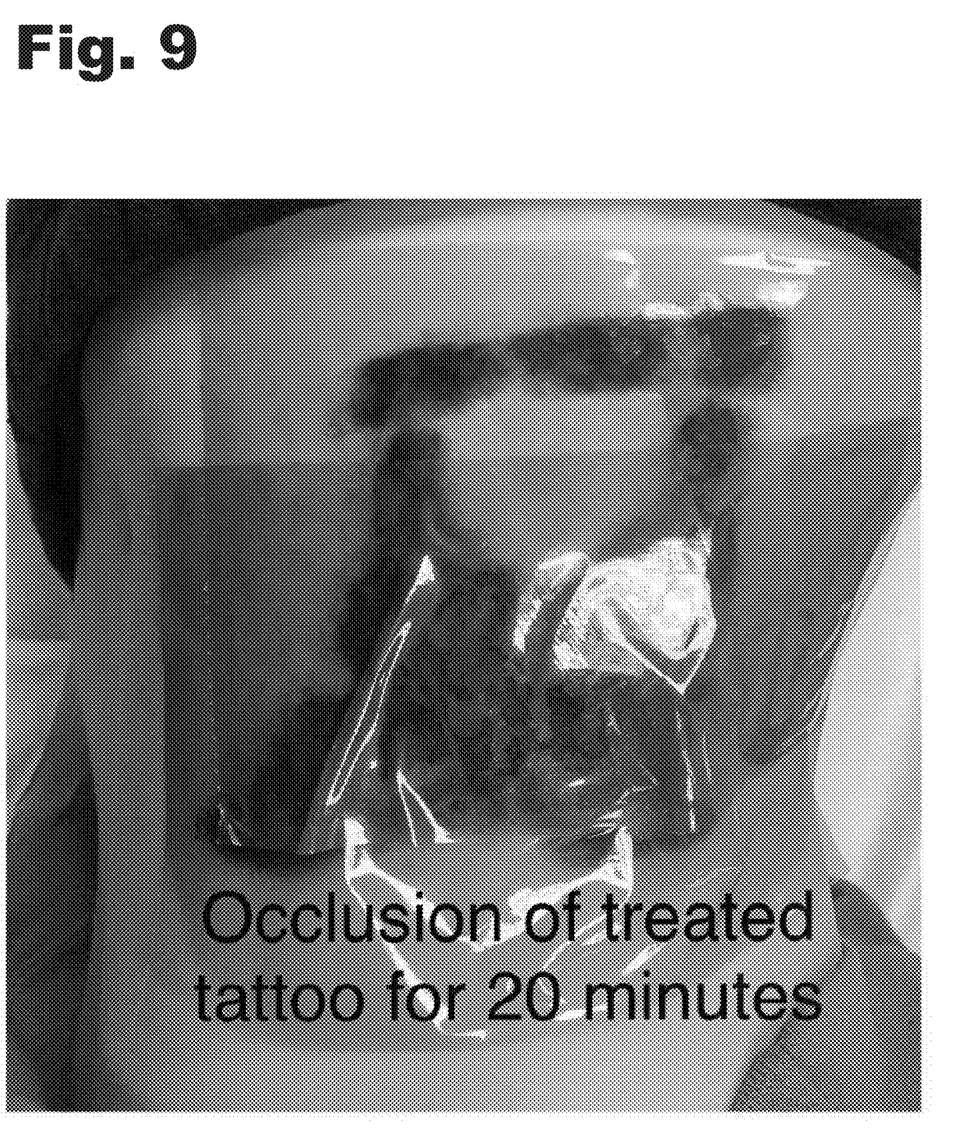

In FIG. 9, a plastic film is applied to treated tattoo. This allows the primary solution to penetrate deeper within the cells. This may be left on for 20 minutes duration.

Figure 10:
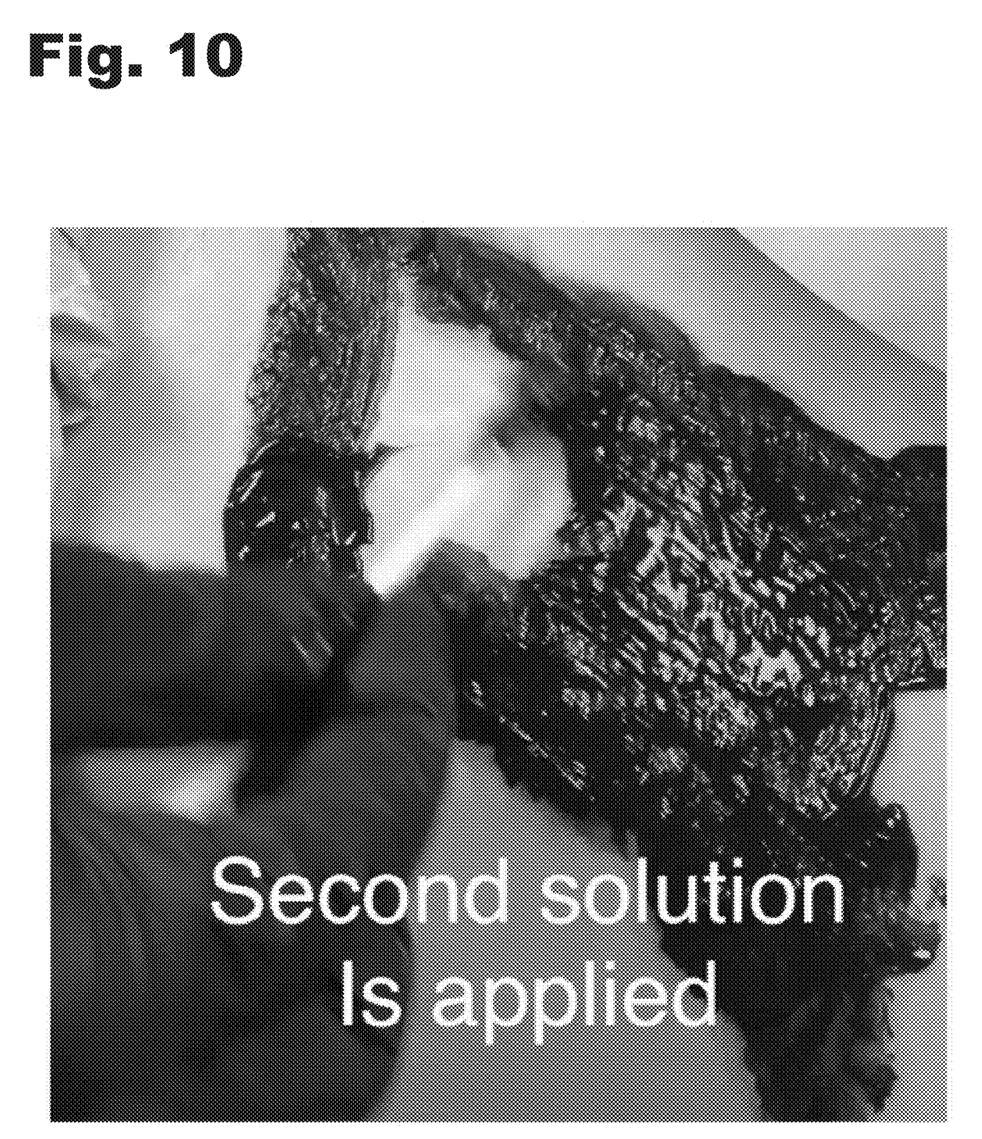

In FIG. 10, after the film and solution are removed, the secondary solution is applied for additional 10 minutes. This secondary solution contains a mixture of charcoal and bentonite clay a very unique combination with extraordinary amounts of absorption properties. The secondary solution enhances the innate healing process through the means of neutralizing cellular inflammation and reduces immediate erythema and edema by enhancing localized oxygen to purifying the wound with the abundance of minerals. This can be an important component for wound healing.

Figure 11:
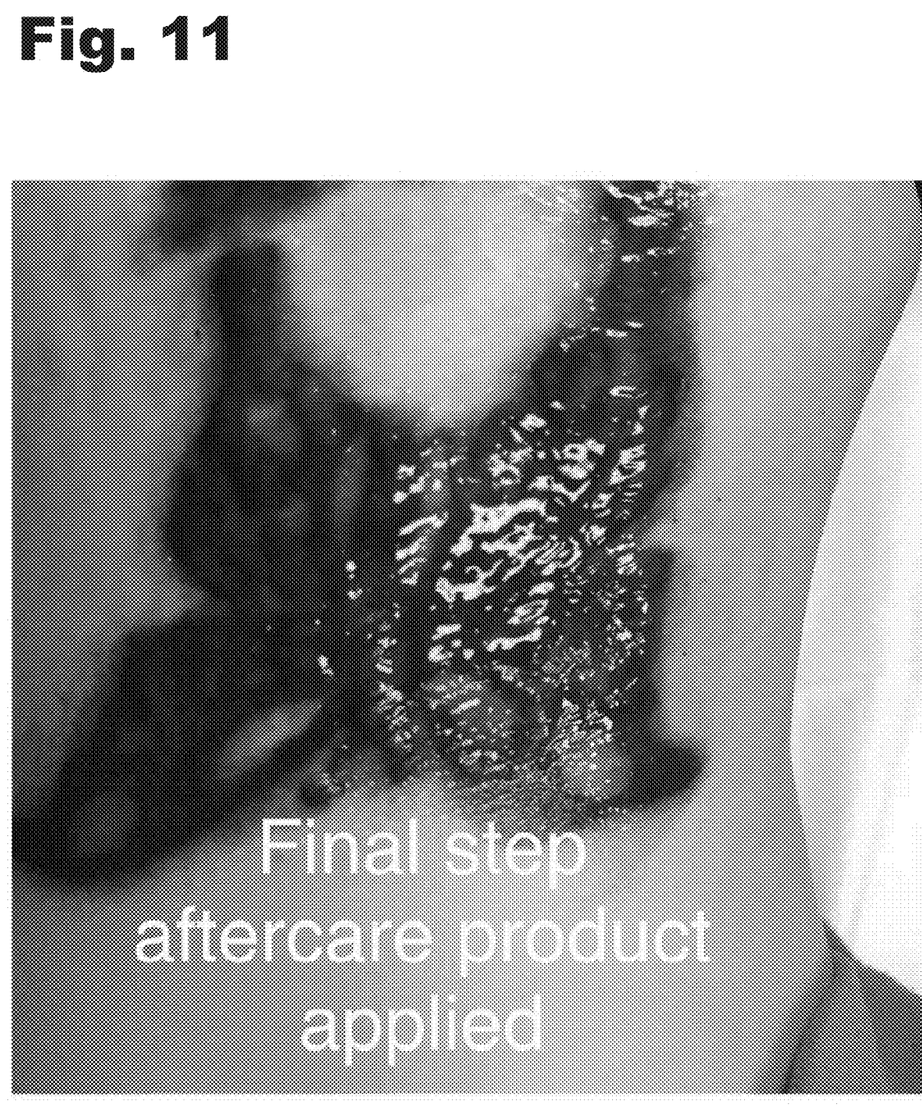

In FIG. 11, after the secondary solution is removed, the appropriate aftercare is applied. For complete removal of the tattoo, this process may take approximately three to six treatments. Variables may include, but are not limited to, the type of ink, age of tattoo ink, previous treatments such as laser, cover up tattoos and overall health of patient.

It is noted that the examples shown and described are provided for purposes of illustration and are not intended to be limiting. Still other examples are also contemplated.

The invention claimed is:

1. A method for removing tattoo ink from a treatment area on skin without scarring, comprising:
    needling the treatment area with a needle dipped into a primary solution of beta glucan;
    continuing to apply the primary solution of beta glucan to the treatment area, the primary solution triggering increased macrophage activity in the skin and stimulating the skin in the treatment area to enhance removal of the tattoo ink from the skin;
    applying a plastic film to the treatment area after applying the primary solution to the treatment area, leaving the plastic film on the treatment area for 20 minutes;
    removing the primary solution after removing the plastic film;
    applying a secondary solution to the treatment area immediately after removing the primary solution, the secondary solution remaining on the treatment area for about 10 minutes, the secondary solution including a negatively charged bentonite clay to bind with positively charged ink molecules, the secondary solution including minerals derived from bentonite clay to reduce infections and healing time, and the secondary solution including charcoal to enhance innate healing by neutralizing cellular inflammation and to reduce immediate erythema and edema by increasing localized oxygen during removing of the tattoo ink; and
    removing the secondary solution.

2. The method of claim 1, wherein the primary solution further includes bentonite clay.

3. The method in claim 1, wherein the primary solution further includes Himalayan Salt.

4. The method in claim 1, wherein the primary solution has a pH of about 8-10.

5. The method in claim 1, wherein the secondary solution has a pH of about 8-10.

6. A method for removing tattoo ink from a treatment area on skin without scarring, comprising:

applying a primary solution of beta glucan and salt solution to the treatment area, the primary solution triggering increased macrophage activity in the skin and stimulating the skin in the treatment area to enhance removal of the tattoo ink from the skin;

removing the primary solution; and coating the treatment area with a secondary solution immediately after removing the primary solution, the secondary solution remaining on the treatment area for 10 minutes, the secondary solution including negatively charged bentonite clay to bind with positively charged ink molecules, the secondary solution including minerals derived from bentonite clay to reduce infections and healing time, and the secondary solution including charcoal to enhance innate healing by neutralizing cellular inflammation and to reduce immediate erythema and edema by increasing localized oxygen during removing of the tattoo ink.

7. The method in claim 6, wherein at least one of the primary solution and the secondary solution includes Himalayan Salt.

8. The method in claim 6, wherein at least one of the primary solution and the secondary solution has a pH of about 8-10.

9. A method for removing tattoo ink from a treatment area on skin without scarring, comprising:

applying a topical numbing agent to the treatment area;

disrupting a skin barrier in the treatment area by a needle or ablative device to improve penetration;

needling the treatment area with the needle dipped into a primary solution of beta glucan, the primary solution triggering increased macrophage activity in the skin and stimulating the skin in the treatment area to enhance removal of the tattoo ink from the skin;

applying a plastic film to the treatment area after applying the primary solution to the treatment area, leaving the plastic film on the treatment area for 20 minutes;

removing the primary solution after removing the plastic film;

coating the treatment area with a secondary solution, the secondary solution remaining on the treatment area for 10 minutes, the secondary solution of a negatively charged bentonite clay dissolved in solution to bind with positively charged ink molecules, the secondary solution including trace minerals derived from bentonite clay to reduce infections and healing time, and the secondary solution including charcoal to enhance innate healing by neutralizing cellular inflammation and to reduce immediate erythema and edema by increasing localized oxygen during removing of the tattoo ink.

* * * * *